US010370307B2

(12) United States Patent
Boutrot et al.

(10) Patent No.: US 10,370,307 B2
(45) Date of Patent: Aug. 6, 2019

(54) PROCESS FOR THE OLIGOMERIZATION OF OLEFINS EMPLOYING A CLEANING DEVICE

(71) Applicants: AXENS, Rueil-Malmaison (FR); IFP Energies Nouvelles, Rueil-Malmaison (FR)

(72) Inventors: Catherine Boutrot, Chatou (FR); Nicolas Janot, Suresnes (FR); Xavier Liege, Paris (FR); Etienne Niderkorn, Rueil-Malmaison (FR); Jerome Pigourier, Meudon (FR); Daniel Jean Vinel, Les Mureaux (FR); Frederic Favre, Lyons (FR); Lionel Magna, Lyons (FR)

(73) Assignees: AXENS, Rueil Malmaison (FR); IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 15/850,641

(22) Filed: Dec. 21, 2017

(65) Prior Publication Data

US 2018/0179122 A1    Jun. 28, 2018

(30) Foreign Application Priority Data

Dec. 22, 2016    (FR) .................................... 16 63200

(51) Int. Cl.
*C07C 2/08*    (2006.01)
*C07C 2/04*    (2006.01)
(Continued)

(52) U.S. Cl.
CPC .................. *C07C 2/08* (2013.01); *B01D 3/14* (2013.01); *B01J 19/002* (2013.01); *B01J 19/24* (2013.01);
(Continued)

(58) Field of Classification Search
CPC .... C07C 2/08; C07C 2/04; C07C 2/02; C07C 2/06; C07C 2/10
See application file for complete search history.

(56) References Cited

U.S. PATENT DOCUMENTS

| 8,946,467 B2 * | 2/2015 | Reine ..................... C07C 67/303 560/127 |
| 2012/0142989 A1 * | 6/2012 | Jaber ......................... C07C 2/36 585/532 |

FOREIGN PATENT DOCUMENTS

| KR | 2002050861 A * | 6/2002 | ............. F28G 13/00 |
| KR | 2002050861 A | 6/2002 | |

(Continued)

OTHER PUBLICATIONS

KR2002050861A_English Translation (Year: 2002).*

(Continued)

*Primary Examiner* — Youngsul Jeong
(74) *Attorney, Agent, or Firm* — Millen, White, Zelano and Branigan, P.C.

(57) ABSTRACT

The invention concerns a process for the oligomerization of ethylene into alpha-olefins, comprising a step for the oligomerization of ethylene, a step for deactivation of the catalyst, a and step for separation of the products, the reactor being provided with a cooling loop (100, 101, 102) by means of which at least a portion of the reaction effluent is moved through at least two switchable heat exchangers, said heat exchangers being cleaned alternately by means of an integrated cleaning device.

13 Claims, 1 Drawing Sheet

(51) Int. Cl.
| | |
|---|---|
| *C07C 2/02* | (2006.01) |
| *B01J 19/00* | (2006.01) |
| *B01J 19/24* | (2006.01) |
| *F28G 9/00* | (2006.01) |
| *F28D 15/00* | (2006.01) |
| *B01D 3/14* | (2006.01) |
| *C07C 2/30* | (2006.01) |
| *F28D 21/00* | (2006.01) |
| *C08F 210/16* | (2006.01) |

(52) U.S. Cl.
CPC .............. *B01J 19/2465* (2013.01); *C07C 2/30* (2013.01); *F28D 15/00* (2013.01); *F28G 9/00* (2013.01); *B01J 2219/00103* (2013.01); *B01J 2219/00247* (2013.01); *B01J 2219/00252* (2013.01); *B01J 2231/20* (2013.01); *C08F 210/16* (2013.01); *F28D 2021/0022* (2013.01)

(56) References Cited

FOREIGN PATENT DOCUMENTS

| WO | 2012072178 A1 | 6/2012 | |
|---|---|---|---|
| WO | WO-2012072178 A1 * | 6/2012 | .............. B01J 3/008 |

OTHER PUBLICATIONS

Search Report in Corresponding French Application No. 1663200 dated May 24, 2017.
Pujado et al. "Catylitic Olefin Condensation" Handbook of Petroleum Processing; 2006 pp. 372-399.

* cited by examiner

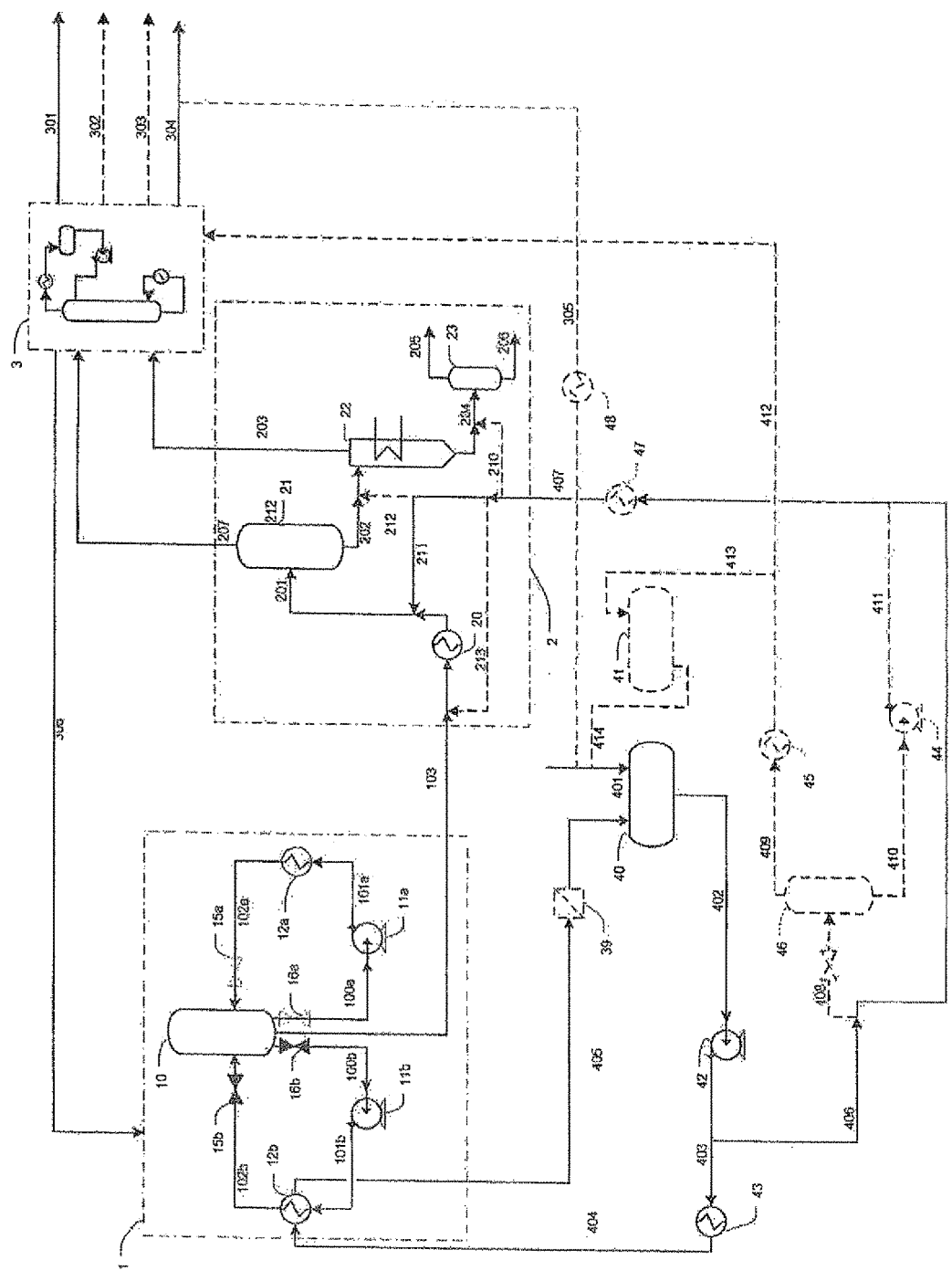

PROCESS FOR THE OLIGOMERIZATION OF OLEFINS EMPLOYING A CLEANING DEVICE

The invention relates to the field of the oligomerization of ethylene. This oligomerization is aimed at producing alpha-olefins used as a co-monomer in processes for the production of polyethylene. The oligomerization reaction is usually carried out in a liquid phase catalysis process. It is also highly exothermic, necessitating external cooling via heat exchangers. Secondary oligomerization reactions are the production of very long oligomers and/or polymers. Most of the time, these polymers cause clogging; in particular, they become deposited on the tubes of the heat exchangers. This necessitates frequent stoppages of the process, in order to isolate and clean the clogged heat exchanger, which has a deleterious effect on the efficiency and operating capability of the process and affects its production costs.

Attempts to alleviate the problems linked to the deposits of polymers in the equipment of the process are known to the person skilled in the art. Such attempts have usually resulted in using various mechanical means such as, for example, cleaning by projecting water under high pressure. That method suffers from the disadvantage of requiring the exchanger to be opened and also requires intense drying of it before the latter is returned to service, because moisture is a known poison in this type of catalysis.

Cleaning using a solvent is possible because polyethylene is soluble in the majority of light hydrocarbons under suitable temperature conditions. The solvent which has acted for the cleaning is then charged with polymers and heavy oligomers as well as with catalyst (or compounds obtained from the catalyst, such as metals). As a consequence, this suffers from the disadvantage of requiring an external supply of solvent in addition to equipment costs relating to the separation of the polymers, the heavy oligomers and catalysts (or compounds obtained from the catalyst) on the one hand and from the solvent on the other hand.

The Applicant's research has led to the development of a novel process for the oligomerization of ethylene which is more efficient and which necessitates fewer stoppages to clean the equipment because of the integrated use of a process for cleaning said equipment of the process or in fact the heat exchangers used in said processes of the olefins oligomerization type.

The invention also concerns a facility for use in the process in accordance with the invention.

SUMMARY OF THE INVENTION

The invention concerns a process for the oligomerization of ethylene into alpha-olefins, comprising:
- a step for oligomerization of the ethylene in a reaction section 1 comprising a reactor 10, in the presence of a catalyst, and optionally a diluent,
- a step for deactivation of the catalyst contained in the reaction effluent,
- a step for evaporation of the products contained in the reaction effluent in order to separate them from the deactivated catalyst, carried out in an evaporation section 2,
- a step for separation of the products contained in the reaction effluent 103 in a separation section 3, said reactor being provided with at least one cooling loop 100 *a/b*, 101*a/b*, 102*a/b*, by means of which the reaction medium is caused to move through at least two switchable heat exchangers which are capable of being connected to at least one cooling loop in a manner such that when at least one heat exchanger is operatively connected to at least one cooling loop, the other disconnected heat exchanger undergoes a step for cleaning by means of a cleaning device in which a solvent which is capable of cleaning said heat exchanger is caused to move in a loop, the cleaning device comprising:
- a storage drum 40 for the cleaning solvent,
- a heat exchanger 43 for heating the cleaning solvent to a temperature above 130° C. in a manner such as to allow the polymer deposited in the disconnected heat exchanger to be dissolved;
- a recirculation pump 42 for moving the cleaning solvent in a loop in the cleaning device between the solvent storage drum 40, the heat exchanger 43 for the solvent and the disconnected heat exchanger which is to be cleaned.

One of the advantages of the process in accordance with the invention is to provide a means for rapidly and efficiently cleaning the process equipment, in particular the exchangers employed, without harming the yield and operating capability of the oligomerization process.

Another advantage of the process is that it is easy to carry out and is integrated with the various steps of the process, in particular by using the cleaning solvent from the process per se.

The process in accordance with the invention may be used to overcome the disadvantages of the prior art by minimizing the equipment costs and/or the loss of productivity and/or by minimizing the consumption of cleaning solvent. It can be used to wash the heat exchanger by dissolving the polymers formed and deposited on the walls of the heat exchanger using a hydrocarbon solvent. It can also be used to integrate the elimination of the heavy oligomers and/or polymers and/or spent catalysts contained in the cleaning solvent in the catalyst deactivation and evaporation section by mixing at least a portion of the cleaning solvent charged with heavy oligomers and/or polymers and/or spent catalysts with the effluent from the oligomerization section.

BRIEF DESCRIPTION OF THE FIGURES

The FIGURE describes a layout of the process which is carried out, with the cleaning device in accordance with the invention when one heat exchanger is operating (12*a*) and the other is being cleaned (12*b*) with the cleaning device.

DETAILED DESCRIPTION OF THE INVENTION

The invention concerns a process for the oligomerization of ethylene into alpha-olefins, comprising:
- a step for oligomerization of the ethylene in a reaction section 1 comprising a reactor 10, in the presence of a catalyst, and optionally a diluent,
- a step for deactivation of the catalyst contained in the reaction effluent 103,
- a step for evaporation of the products contained in the reaction effluent in order to separate them from the deactivated catalyst, carried out in an evaporation section 2,
- a step for separation of the products contained in the reaction effluent in a separation section 3, said reactor being provided with at least one cooling loop 100 *a/b*, 101*a/b*, 102*a/b*, by means of which the reaction medium is caused to move through at least two switchable heat exchangers which are capable of being connected to at least one cooling loop in a manner such that when at least one heat exchanger is operatively connected to at least one cooling loop, the other disconnected heat exchanger undergoes a step for cleaning by means of a cleaning device in which a solvent which is capable of cleaning said heat exchanger is caused to move in a loop, the cleaning device comprising:

a storage drum 40 for the cleaning solvent, a heat exchanger 43 for heating the cleaning solvent to a temperature above 130° C. in a manner such as to allow the polymer deposited in the disconnected heat exchanger to be dissolved;

a recirculation pump 42 for moving the cleaning solvent in a loop in the cleaning device between the cleaning solvent storage drum 40, the heat exchanger 43 for the cleaning solvent and the disconnected heat exchanger which is to be cleaned.

Advantageously, in accordance with the invention, at least a portion of the cleaning solvent obtained from the solvent loop of the cleaning device 406, 407 is sent to the product evaporation step in the evaporation section 2.

For the purposes of clarity, the invention will be described in the remainder of the text with reference to the FIGURE which describes an illustrative layout of the process. Reference to the FIGURE should not in any case limit the scope of the process.

The cleaning solvent which has been used for cleaning, which contains heavy oligomers and/or polymer and/or spent catalyst, is termed the "charged cleaning solvent" in the remainder of the text.

Reaction Section 1

In accordance with the invention, the process for the oligomerization of ethylene into alpha-olefins comprises a step for the oligomerization of ethylene carried out in the presence of a catalyst in a reaction section 1 comprising a reactor 10. Advantageously, the reaction for the oligomerization of ethylene is a liquid phase catalysis process, generally homogeneous, carried out in the presence or absence of a diluent, using a Ziegler type catalyst which generally comprises a compound of a metal such as titanium, chromium, zirconium and at least one organoaluminium compound. The reaction is preferably carried out at a temperature in the range from ambient temperature to 200° C., preferably in the range 30° C. to 170° C., and at a pressure in the range 0.5 to 20 MPa, preferably in the range 1.0 to 10 MPa. This oligomerization reaction is sometimes carried out in an inert diluent such as ortho-xylene or cyclohexane.

In the general context of the invention, the ethylene oligomerization process may be a process for the dimerization of ethylene into 1-butene, a process for the trimerization of ethylene into 1-hexene or a process for the tetramerization of ethylene into 1-octene.

Reactions for the oligomerization of ethylene are exothermic. The heat generated by the reaction has to be extracted in order to prevent an uncontrolled rise in the temperature of the reaction medium. Depending on the temperature level reached, the consequences may be a loss of selectivity by thermal degradation of the catalyst and of the reaction products. The heat of reaction generated in the reactor is extracted by using at least one cooling loop (conduits 100 *a/b*, 101*a/b*, 102*a/b*) comprising at least one heat exchanger 12 *a/b*.

The reaction effluent 103 obtained from the reaction section 1 for the oligomerization of ethylene comprises unconverted ethylene, alpha-olefins such as 1-butene, 1-hexene, or 1-octene, and other C4 to C30+ reaction products (i.e. containing in the range 4 to more than 30 carbon atoms per molecule), as well as any diluent for the oligomerization reaction. Said effluent also comprises at least a portion of the catalyst. The reaction effluent 103 may be moved in a heat exchanger 20 in which it is vaporized in the evaporation section 2.

In the particular case of an ethylene dimerization process, this vaporization in the heat exchanger 20 is preferably carried out at a pressure which is equal to or substantially identical to that of the ethylene dimerization step and at a temperature of 80° C., which means that at least one gas phase and at least one liquid phase can be separated in the evaporation section 2, in particular in one or more flash drums for the evaporation section 2.

Deactivation and Evaporation Section 2

In accordance with the invention, in general, at the outlet from the reaction section 1 for oligomerization, the catalyst contained in the effluent 103 undergoes a deactivation step, preferably carried out upstream of the evaporation section 2. This deactivation is carried out using any compound which is known to the person skilled in the art to have an inhibiting activity on the oligomerization catalyst. An example is a polar oxygen-containing or nitrogen-containing compound which is intended to deactivate substantially the whole of the catalyst present in the effluent 103. Examples of nitrogen-containing catalyst inhibitors of this type have been described in European patent EP 0 200 654 B.

The catalyst inhibitor used in the deactivation step is generally selected from amines, preferably from primary or secondary amines with general formula $R_1R_2NH$, in which $R_1$ is hydrogen or a hydrocarbyl radical and $R_2$ is a hydrocarbyl radical, or linear or branched alcohols preferably containing 2 to 20 carbon atoms, more preferably 5 to 15 carbon atoms or carboxylic acids such as n-octanoic acid or water or ammonia.

When the catalyst inhibitor is selected from amines, an inhibitor selected from the following compounds or mixtures thereof is preferably used: cyclohexylamine, ethyl-2-hexylamine, arylamine, stearylamine, oleylamine, aniline, N-methyl aniline, dibutylamine, didecylamine, and mixtures of amines obtained from natural fats such as tallow, palm oil or coprah oil.

When the catalyst inhibitor is selected from alcohols, a linear or branched alcohol containing 2 to 20 carbon atoms is used such as, for example, 1-hexanol, 2-hexanol, 3-hexanol, 2-methyl-1-hexanol, 2-ethyl-1-hexanol, 1-heptanol, 2-heptanol, 2-methyl-3-heptanol, 1-octanol, 2-octanol, 3-octanol, 1-decanol, 2-decanol, 3-decanol, or 2-ethyl-1-decanol; a diol such as, for example, ethylene glycol, propane diols, butane diols or in fact a polyol such as glycerol, used alone or as a mixture. Preferably, 2-ethyl-1-hexanol is used.

When the catalyst inhibitor is selected from carboxylic acids, a linear or branched acid containing 2 to 20 carbon atoms is used such as, for example, acetic acid, propionic acid, butyric acid, pentanoic acid (valeric acid), hexanoic acid, or 2-ethylhexanoic acid, octanoic acid (caprylic acid), dodecanoic acid, stearic acid, benzoic acid, 2-hydroxybenzoic acid, used alone or as a mixture. Preferably, 2-ethylhexanoic acid and octanoic acid (caprylic acid) are used.

After the catalyst deactivation step, in accordance with the invention, the reaction effluent obtained from the deactivated reactor 103 (deactivation step not shown in the FIGURE) undergoes an evaporation step in order to separate, on the one hand, the deactivated catalyst as well as the heavy by-products from the reaction and, on the other hand, unconverted ethylene, the products formed as well as any diluent. This evaporation step is preferably carried out by vaporization of a portion of the reaction effluent in order to obtain one or more vapour phases containing unconverted ethylene, the products formed and any diluent. This or these vapour phases are advantageously sent (see conduits 203, 207) to the separation section 3 in which the various products of interest which are formed are separated from each other.

In accordance with the invention, in the step for evaporation of the products contained in the reaction effluent 103 carried out in the evaporation section 2, the catalyst is separated from the set of the products from the reaction.

In a variation of the process of the invention, the evaporation section 2 may comprise at least one flash drum 21, 23 (drums/separators with liquid-vapour equilibrium) and at least one vaporizer or thin film or falling film evaporator 22 for vaporizing the desired product.

In the particular case of an ethylene dimerization process, the reaction effluent 103, preferably obtained from the heat exchanger 20, alone or as a mixture with at least a portion of the cleaning solvent obtained from the stream 406-407 (stream 211, 201) may be vaporized in a first flash drum 21 under conditions which can separate a gas phase 207 essentially containing 1-butene and other C6 and C8 hydrocarbon products and ethylene, and a second liquid phase 202 containing the deactivated catalyst. In one embodiment, it is possible for at least a portion of the cleaning solvent obtained from the stream 406-407 (stream 213) to be sent as a mixture with the effluent 103 upstream of the heat exchanger 20. Advantageously, at least a portion of the liquid phase 202, alone or as a mixture with at least a portion of the cleaning solvent obtained from the stream 406-407 (stream 212) may then be directed to a vaporizer or thin film evaporator 22 in which it is evaporated under conditions which allow a gas phase essentially containing 1-butene and possibly heavier hydrocarbon products and a liquid phase enriched in concentrated deactivated catalyst 204 to be separated. The rate of evaporation in the thin film or falling film evaporator is generally of the order of 99% by weight with respect to the liquid phase entering the evaporator. At least a portion of the liquid phase enriched in concentrated deactivated catalyst 204, alone or mixed with at least a portion of the cleaning solvent obtained from the stream 406-407 (stream 210) is advantageously depressurized and flashed in a flash drum 23, generating a vapour phase 205 which is substantially free from polymer and deactivated catalyst, and a liquid phase 206 which is concentrated in polymers and deactivated catalyst 206. Advantageously, the gas phases 207, 203 obtained from the evaporation step carried out in the evaporation section 2 and essentially containing 1-butene and ethylene as well as heavier hydrocarbon products are condensed in the form of a liquid product which is sent to the separation step carried out in the separation section 3 in which the various products will be separated from each other.

In the particular case of an ethylene trimerization process, the reaction effluent from the reactor is preferably sent to the deactivation and evaporation section 2 advantageously comprising flash drums. The catalyst in the reaction effluent may be deactivated by injecting 2-ethylhexanol used as an inhibitor. The mixture may be produced by using a dynamic in-line mixer (not shown in the FIGURE). In particular, the reaction medium obtained from the reactor may be decompressed in a first flash drum at a pressure which is preferably 2.4 MPa. Said depressurized reaction medium may then be vaporized by heating to a temperature which is preferably 175° C. This vaporization is carried out in a heat exchanger. The vapour phase is then separated from the liquid phase in a drum. The vapour phase is sent to the separation section 3. The liquid phase from the first flash drum is depressurized in a second flash drum at a pressure which is preferably 1.1 MPa. Said depressurized liquid phase is then vaporized by heating to a temperature which is preferably 175° C. This vaporization is carried out in a heat exchanger. The vapour phase is then separated from the liquid phase in a drum. The vapour phase is sent to the separation section 3 and the liquid phase from the second flash drum is depressurized at a pressure which is preferably 0.2 MPa. Said depressurized liquid phase is then vaporized by heating to a temperature which is preferably 200° C. This vaporization is preferably carried out in a thin layer evaporator. The deactivated catalyst as well as its heavy by-products separated in the deactivation and evaporation section 2 are pumped and sent to an incinerator.

Separation Section 3

In the general context of the invention, which concerns a process for the oligomerization of olefins, the separation step is advantageously carried out in the separation section 3 which separates the various products formed in the olefin oligomerization reaction.

The oligomeric olefins obtained from the oligomerization of ethylene have a molecular weight which is higher than the ethylene which has not reacted. In general, the ethylene which has not reacted has a lower boiling point than that of the oligomeric olefins obtained from the reaction. Any means for separation which is known to the person skilled in the art which exploits the differences in volatility and molecular weight between the products to be separated may be employed. Advantageously, in accordance with the invention, the separation means employed in the separation step in the separation section 3 are distillation columns of any type.

In the case of a process for the dimerization of ethylene, unreacted ethylene alone (stream 306), 1-butene (stream 301) and the C6+ hydrocarbon products (stream 304) are preferably separated.

In the case of a process for the trimerization of ethylene, unreacted ethylene (stream 306) is preferably separated from the products of interest such as 1-hexene and possibly diluent (stream 301 and optionally 302, 303, etc) and the heavier fractions (stream 304).

The separation section 3 is advantageously provided with several distillation columns (not shown in the FIGURE).

Advantageously, in accordance with the invention, the unreacted ethylene separated in the separation step in the separation section 3 is recycled to the reactor (stream 306).

In the particular case of a process for the trimerization of ethylene, the separation section 3 may comprise at least four distillation columns disposed as follows: a first distillation column in which the unconverted ethylene is separated into a head fraction and into a bottom fraction containing the remainder of the compounds; a second distillation column in which the bottom fraction obtained from the first column is separated into a head fraction comprising 1-hexene and 1-butene and into a bottom fraction. Said bottom fraction is principally composed of diluent; a third distillation column in which the head fraction from the second distillation is separated into a head fraction principally comprising 1-butene and into a bottom fraction principally comprising 1-hexene, the reaction product; a fourth column in which the bottom fraction from the second distillation is separated into a head fraction principally comprising diluent which may be recycled to the reactor and into a bottom fraction comprising heavier products, in particular C8+(containing 8 or more carbon atoms). The deactivated catalyst as well as the heavy by-products are evacuated.

In a variation of the process in accordance with the invention, the cleaning solvent is constituted by diluent. In a variation of the process in accordance with the invention, the cleaning solvent is constituted by the bottom fraction comprising the heavier products, in particular C8+ obtained from the fourth column. In a variation of the process in accordance with the invention, the cleaning solvent is constituted by the bottom product obtained from the second column.

Cleaning Section for Heat Exchanger 12a/12b

In accordance with the invention, the reactor used in the reaction section 1 is provided with a cooling loop 100 a/b, 101a/b, 102a/b, by means of which at least the reaction medium is moved through at least two heat exchangers in order to extract the heat generated by the oligomerization reaction and avoid an uncontrolled rise in the temperature of the reaction medium in the reactor.

In accordance with the invention, the heat exchangers 12a, 12b used are switchable and are capable of being connected to at least one cooling loop in a manner such that when at least one heat exchanger is operating and connected to at least one cooling loop, the other heat exchanger is disconnected and a step for cleaning is carried out by means of a cleaning device in which a solvent which is capable of cleaning said heat exchanger is caused to move in a loop, the cleaning device comprising:

a storage drum 40 for the cleaning solvent,
a heat exchanger 43 for heating the cleaning solvent to a temperature above 130° C., preferably to above 150° C., more preferably to above 170° C., yet more preferably to above 180° C., in a manner such as to allow the polymer deposited in the disconnected heat exchanger to be dissolved;
a recirculation pump 42 for moving the cleaning solvent in a loop in the cleaning device between the cleaning solvent storage drum 40, the heat exchanger 43 for the cleaning solvent and the disconnected heat exchanger which is to be cleaned.

Cleaning is carried out by moving the hot solvent with the aid of a recirculation pump 42 via the conduits 402, 403, 404, 405.

In accordance with the invention, the pressure of the solvent storage drum 40 is preferably fixed in a manner such as to maintain the cleaning solvent in the liquid form. This pressure is preferably in the range 0.5 to 3 MPa.

The process in accordance with the invention may employ several heat exchangers 12a, 12b which are capable of being connected to at least one cooling loop in order to extract the heat generated by the oligomerization reaction. Preferably, 2 or 3 or 4 or 5 heat exchangers may be employed. The FIGURE has two cooling loops each comprising one heat exchanger, used in alternation. The valves 15a/16a are open and connected to the reactor 10 when the heat exchanger 12a is operating with the cooling loop 100a, 101a, 102a. During this time, the valves 15a/16a are closed, thereby isolating the second cooling loop 100b, 101b, 102b of the reactor 10 and allowing it to be cleaned with the cleaning device.

The cleaning solvent is advantageously selected from saturated hydrocarbons such as butane, isobutane, pentane, cyclohexane, methylcyclohexane, n-hexane, heptane, octane, decane, or dodecane; unsaturated hydrocarbons such as a monoolefin or a diolefin containing 4 to 20 carbon atoms, for example; aromatic hydrocarbons such as benzene, toluene, ortho-, meta- or para-xylene, cumene, mesitylene, ethylbenzene; a gasoline, diesel or kerosene cut; isoparaffins such as Isopar E or C; used alone or as a mixture. The cleaning solvent may be obtained from the process itself, in particular from the separation section 3. Preferably, at least a portion of the cleaning solvent, or even all of the cleaning solvent, originates from the separation step in the separation section 3 (stream 305). Preferably, at least a portion of the cleaning solvent, or even the entirety of the cleaning solvent, originates from fractions of heavier compounds and/or from any diluent separated from the separation step of the separation section 3.

In a variation of the invention, a filter 39 may be implemented on the loop for moving cleaning solvent 402, 403, 404, 405. This filter may be used to capture any possible pieces of polymers which could have been detached from the heat exchanger which are cleaned off without being completely dissolved.

Advantageously, in accordance with the invention, at least a portion of the charged cleaning solvent obtained from the solvent loop of the cleaning device 406 is sent to the step for evaporation of the products in the evaporation section 2.

As an example, once the polymer has been dissolved in the cleaning solvent, at least a portion of the charged cleaning solvent may be directed towards the step for evaporation of the products, in particular to the evaporation section 2 (see the conduits 406, 407, 211, 212, 210 and 213 in the FIGURE).

In a variation of the process, once the polymer has been dissolved in the cleaning solvent, at least a portion of the charged cleaning solvent (406-407) is sent to the evaporation section 2 as a mixture with a portion of the reaction effluent 103, either upstream (stream 213) or downstream (stream 211) of the heat exchanger 20 when this heat exchanger is present.

In a variation of the process, once the polymer has been dissolved in the cleaning solvent, at least a portion of the charged cleaning solvent (406-407) is sent as a mixture with the liquid phase 202 obtained from the flash drum 21 (stream 212) employed in the evaporation section 2.

In a variation of the process, once the polymer has been dissolved in the cleaning solvent, at least a portion of the charged cleaning solvent (406-407) is sent as a mixture with the liquid phase 204 obtained from the vaporizer or from the thin film evaporator 22 (stream 210) employed in the evaporation section 2.

The concentration of polymers and heavy oligomers in the charged cleaning solvent is advantageously less than 5% by weight, preferably less than 1% by weight with respect to the cleaning solvent.

In a variation of the invention, once the polymer has been dissolved in the cleaning solvent, at least a portion of the charged cleaning solvent, preferably removed from the stream 406, 408, is depressurized and directed towards a partial vaporization step by means of a flash drum 46, in order to produce at least one vapour phase 409 and at least one liquid phase 410. The partial vaporization resulting from this depressurization has two advantages. Firstly, it can be used to generate a vapour phase with a polymers, heavy oligomers and catalyst content which is sufficiently low to allow it to be directed directly to the separation section 3 of the process after any optional condensation in the exchanger 45 (line 409, 412). After condensation in the exchanger 45, at least a portion of this vapour phase may also be collected in the receiving drum 41 then returned to the solvent storage drum 40 (stream 413, 414) in order to act once again for cleaning the exchanger in accordance with the process of the invention.

Furthermore, this partial vaporization may be used in order to reduce the temperature of the stream 410/411 of the liquid phase recovered from the flash drum 46 in a manner such as to be able to reinject it, preferably as a mixture with the stream 407, into the evaporation section 2 without necessitating cooling. In fact, too high a temperature in the downstream sections of the reactor before completely separating the catalyst, even when it is deactivated, may result in degradation of the products. In such an implementation, a recirculation pump 44 may be implemented between the streams 410 and 411. It is also possible to employ a heat exchanger in the conduit 407 (47).

The partial vaporization of the charged cleaning solvent is preferably carried out by means of a depressurization because using a heat exchanger would involve a high risk of clogging the latter.

In accordance with a further variation of the process of the invention, at least a portion of the cleaning solvent comes from the step for separation in the separation section 3 (stream 305). Preferably, at least a portion of the cleaning solvent originates from fractions of heavier compounds and/or from an optional diluent separated in the separation step, thereby avoiding the necessity for an external supply of cleaning solvent. Preferably, the cleaning solvent is exclusively constituted by heavier hydrocarbon products, recovered in the separation section 3 (stream 304). A fraction of the heavier hydrocarbon products may be directed (305) towards the storage drum 40 for the cleaning solvent. In this manner, no external supply of solvent is required. The conduit 305 may be provided with a heat exchanger 48.

The invention also concerns a facility employing the process in accordance with the invention.

The facility in accordance with the invention comprises:
a reaction section 1 comprising a reactor 10,
a section 2 for evaporation of the reaction effluent,
a separation section 3,
said reactor being provided with at least one cooling loop 100a/b, 101a/b, 102a/b by means of which the reaction medium is caused to move through at least two switchable heat exchangers which are capable of being connected to at least one cooling loop in a manner such that when at least one heat exchanger is operatively connected to at least one cooling loop, the other disconnected heat exchanger undergoes a step for cleaning by means of a cleaning device in which a solvent which is capable of cleaning said heat exchanger is caused to move in a loop, the cleaning device comprising:
   a storage drum 40 for the cleaning solvent,
   a heat exchanger 43 for heating the cleaning solvent to a temperature above 130° C. in a manner such as to allow the polymer deposited in the disconnected heat exchanger to be dissolved;
   a recirculation pump 42 for moving the cleaning solvent in a loop in the cleaning device between the cleaning solvent storage drum 40, the heat exchanger 43 for the cleaning solvent and the disconnected heat exchanger which is to be cleaned.

Advantageously, the cleaning device is connected to the evaporation section 2 via at least one conduit which may be used to send at least a portion of the cleaning solvent to said section 2 for evaporation of the reaction effluent.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1663200, filed Dec. 22, 2016 are incorporated by reference herein.

Example 1: Application of the Process in Accordance with the Invention to a Process for the Dimerization of Ethylene 1-butene was produced by homogeneous catalytic dimerization in the liquid ethylene phase. The device in accordance with the invention as described in the FIGURE was employed. The catalyst was obtained by the interaction of n-butyl titanate, tetrahydrofuran and triethylaluminium as described in Example 1 of the patent EP 0 135 441.

During the ethylene dimerization reaction, the pressure of the reactor 10 was 2.2 MPa and the temperature was 53° C.

The reactor was cooled using two cooling loops each comprising a heat exchanger (12a and 12b). The switchable heat exchanger 12b was disconnected after a 2 month operating period. In the example, it was assumed that cleaning of this exchanger 12b would be carried out while the exchanger 12a was operating.

The reaction effluent 103 contains ethylene, the 1-butene produced as well as certain C6 and C8+ hydrocarbon products (principally octenes) formed during secondary reactions in the reactor 10. The reaction effluent 103 was introduced into the deactivation and evaporation section 2. The reaction effluent 103 was brought into contact with decylamine used as an inhibitor for the catalyst. The section 2 comprised a heat exchanger 20 in which the reaction effluent 103 was vaporized at a pressure of 2.1 MPa and at a temperature of 80° C. then sent to the flash drum 21 in order to separate a gas phase 207 essentially containing 1-butene and ethylene and a second liquid phase 202 containing the deactivated catalyst. Next, the liquid phase 202 obtained from the flash drum 21 was directed into a thin film vaporizer 22 in which it was evaporated at a pressure substantially identical to that of the flash drum 21, under conditions allowing the separation of a gas phase 203 containing ethylene, 1-butene, as well as heavier hydrocarbon products (C6+), and a liquid phase enriched in concentrated deactivated catalyst 204. This liquid phase 204 obtained was depressurized and flashed in a flash drum 23, generating a vapour phase 205 substantially free from polymer and deactivated catalyst, and a liquid phase 206 concentrated with polymers and deactivated catalyst. The compositions of the streams obtained from the deactivation and evaporation section are described in Table 1 below.

| % by weight | Reaction effluent (103) | Gas phase (207) | Gas phase (203) | Gas phase (205) | Liquid, third flash (206) |
|---|---|---|---|---|---|
| Methane | 0.47 | 0.92 | 0.11 | 0.00 | 0.00 |
| Ethylene | 12.03 | 20.69 | 5.41 | 0.00 | 0.00 |
| Ethane | 0.90 | 1.46 | 0.48 | 0.00 | 0.00 |
| 1-butene | 80.84 | 74.59 | 86.03 | 83.33 | 27.27 |
| n-Butane | 0.12 | 0.10 | 0.13 | 0.00 | 0.00 |
| Hexenes | 5.08 | 2.10 | 7.21 | 16.67 | 27.27 |
| Hexane | 0.30 | 0.10 | 0.42 | 0.00 | 4.55 |
| C8+ | 0.16 | 0.03 | 0.21 | 0.00 | 9.09 |
| Triethylaluminium | 0.00 | 0.00 | 0.00 | 0.00 | 0.00 |
| Decylamine | 0.01 | 0.00 | 0.00 | 0.00 | 4.55 |
| Deactivated catalyst | 0.09 | 0.00 | 0.00 | 0.00 | 27.27 |

The various vapour phases 207 and 203 obtained from the flash drum 21 and from the thin film vaporizer 22, substantially free from deactivated catalyst, were condensed in the form of a liquid product which could be sent to a distillation section corresponding to the separation section 3 in which the various products would be separated. In the distillation section 3, ethylene on the one hand and 1-butene plus heavier compounds on the other hand were separated in a second distillation column (not shown). The fraction enriched in ethylene was recycled to the reactor (stream 306). The separation between the 1-butene (stream 301) and the heavier compounds (C6+, stream 304) was carried out in a second distillation column (not shown).

In order to clean the exchanger 12b, the device in accordance with the invention was employed. The cleaning solvent used was n-hexane. Movement (lines 402, 403, 404, 405) of the cleaning solvent was established with the aid of a pump 42 between the solvent storage drum 40 and the exchanger 12b to be cleaned. A heat exchanger 43 on this loop could be used to heat the solvent to a temperature of 180° C.

The pressure of the storage drum 40 for the cleaning solvent (n-hexane) was approximately 1.4 MPa absolute in order to maintain it in the liquid form. Once cleaning had been completed, the solvent charged with polymer and catalyst residues was directed via the lines 406, 407 and 211 towards the flash drum 21.

The process was carried out continuously and meant that opening the equipment could be avoided, in particular the heat exchangers in order to clean them; this represents a saving in labour and avoids the risk of an accident.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for oligomerization of ethylene into alpha-olefins, comprising:
    oligomerizing the ethylene in a reaction section (1) comprising a reactor (10), in the presence of a catalyst, and optionally a diluent, to produce a reaction effluent,
    deactivating the catalyst contained in the reaction effluent,
    evaporating in an evaporation section (2) the reaction effluent in order to separate a portion of the reactant effluent from the deactivated catalyst, and
    separating in a separation section (3) products contained in the reaction effluent,
    said reactor being provided with at least one cooling loop (100 a/b, 101 a/b, 102a/b), by which reaction medium is caused to move through at least two switchable heat exchangers which are capable of being connected to the at least one cooling loop in a manner such that when at least one heat exchanger is operatively connected to the at least one cooling loop, the other heat exchanger is disconnected and undergoes cleaning by a cleaning device in which a cleaning solvent which is capable of cleaning said heat exchanger is caused to move in a loop of solvent of the cleaning device, the cleaning device comprising:
    a cleaning solvent storage drum (40);
    a heat exchanger (43) heating the cleaning solvent to a temperature above 130° C. in a manner such as to allow the polymer deposited in the disconnected heat exchanger to be dissolved thereby producing a charged solvent; and
    a recirculation pump (42) moving the cleaning solvent in the loop of solvent of the cleaning device through the cleaning solvent storage drum (40), the heat exchanger (43) and the disconnected heat exchanger which is to be cleaned,
    wherein the process further comprises sending at least a portion of cleaning solvent obtained from the loop of solvent of the cleaning device to the evaporation section (2).

2. The process as claimed in claim 1, in which the reaction effluent is moved in a heat exchanger (20) in which reaction effluent is vaporized in the evaporation section (2).

3. The process as claimed in claim 1, in which the unreacted ethylene separated in the separation section (3) is recycled to the reactor.

4. The process as claimed in claim 1, in which the heat exchanger (43) heats the cleaning solvent to a temperature of more than 150° C. in a manner such as to dissolve polymer deposited in the disconnected heat exchanger.

5. The process as claimed in claim 1, in which the charged solvent has a concentration of polymers and heavy oligomers less than 5% by weight with respect to the cleaning solvent.

6. The process as claimed in claim 1, in which the cleaning solvent is a saturated hydrocarbon; unsaturated hydrocarbon; aromatic hydrocarbon; a gasoline, diesel or kerosene cut; or an isoparaffin; used alone or as a mixture.

7. The process as claimed in claim 1, in which at least a portion of the cleaning solvent comes from the separation in the separation section (3).

8. The process as claimed in claim 1, in which at least a portion of the cleaning solvent originates from heavier compound fractions and/or from an optional diluent separated from the separation section (3).

9. The process as claimed in claim 1, in which a filter (39) is employed on the loop of solvent of the cleaning device for moving cleaning solvent (402, 403, 404, 405).

10. The process as claimed in claim 1 in which, once the polymer has been dissolved in the cleaning solvent, at least a portion of charged cleaning solvent is depressurized and directed towards a partial vaporization step by means of a flash drum 46, in order to produce at least one vapor phase 409 and at least one liquid phase 410.

11. The process as claimed in claim 1, in which the ethylene oligomerization process is a process for dimerization of ethylene to 1-butene.

12. The process as claimed in claim 1, in which the ethylene oligomerization process is a process for the trimerization of ethylene to 1-hexene.

13. The process as claimed in claim 1, in which the ethylene oligomerization process is a process for tetramerization of ethylene to 1-octene.

* * * * *